United States Patent [19]

Mickiewicz et al.

[11] Patent Number: 4,582,063

[45] Date of Patent: Apr. 15, 1986

[54] TRANSCUTANEOUS NERVE STIMULATION DEVICE WITH SENTINEL

[75] Inventors: Stanley P. Mickiewicz, Stoughton; Alan Coombes, Hingham, both of Mass.

[73] Assignee: Codman & Shurtleff, Inc., Randolph, Mass.

[21] Appl. No.: 617,429

[22] Filed: Jun. 5, 1984

[51] Int. Cl.$^4$ ............................................. A61N 1/32
[52] U.S. Cl. .................................................. 128/421
[58] Field of Search .................. 128/419 R, 421–423, 128/731, 695, 696

[56] References Cited

U.S. PATENT DOCUMENTS

| 3,859,988 | 1/1965 | Lencioni, Jr. | 128/731 |
| 4,068,669 | 1/1978 | Niemi | 128/419 R |
| 4,088,141 | 5/1978 | Niemi | 128/421 |
| 4,235,242 | 11/1980 | Howson et al. | 128/695 |

Primary Examiner—William E. Kamm
Attorney, Agent, or Firm—W. Brinton Yorks, Jr.

[57] ABSTRACT

A sentinel system is provided for a transcutaneous nerve stimulation device in which a sentinel pulse of known characteristics is produced at the device output prior to the production of a stimulation pulse. The output response is measured during the time of sentinel pulse production, and a sentinel warning signal is produced if an undesired output response is measured to alert the user to a potentially hazardous condition.

7 Claims, 13 Drawing Figures

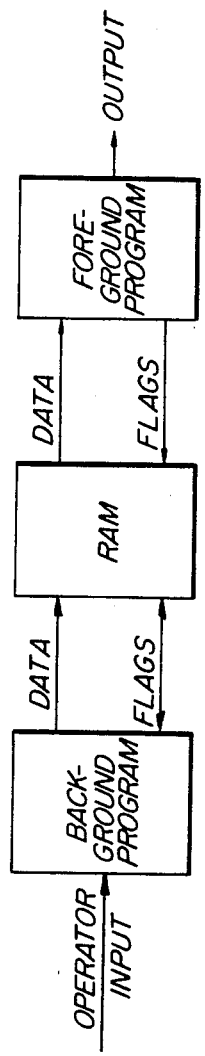

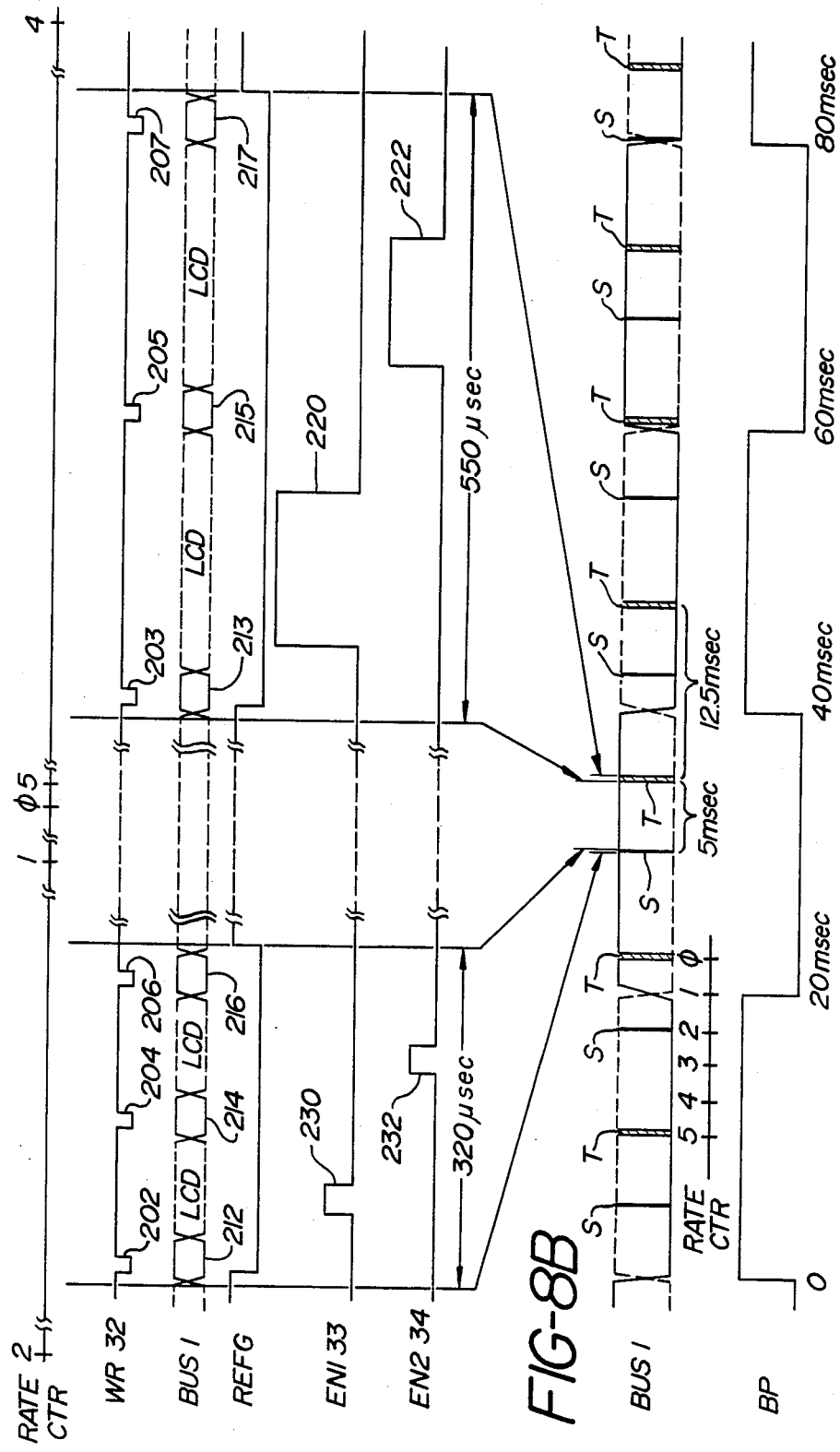

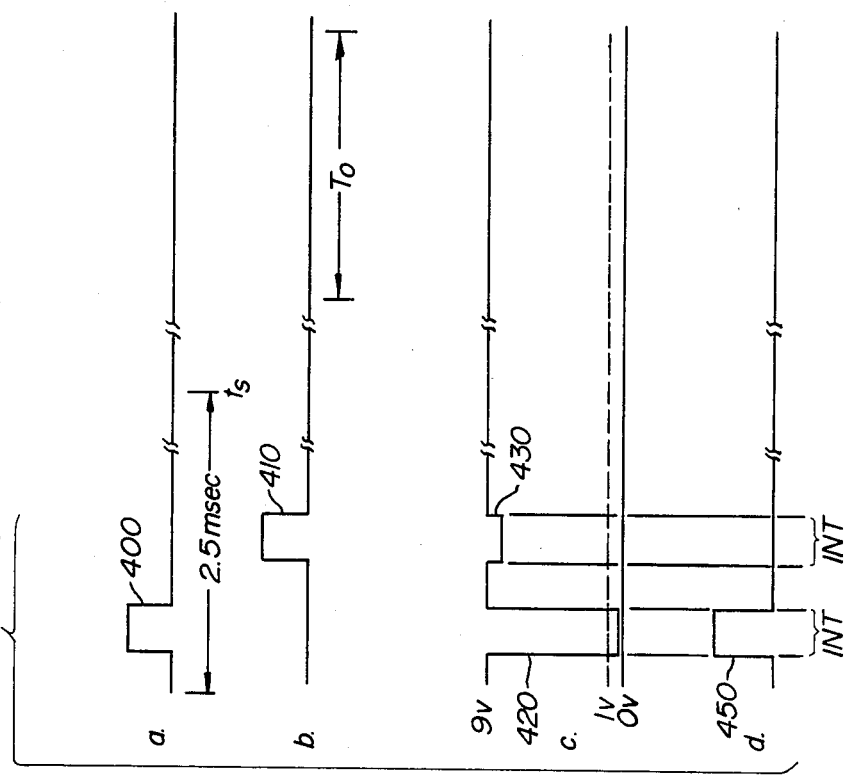
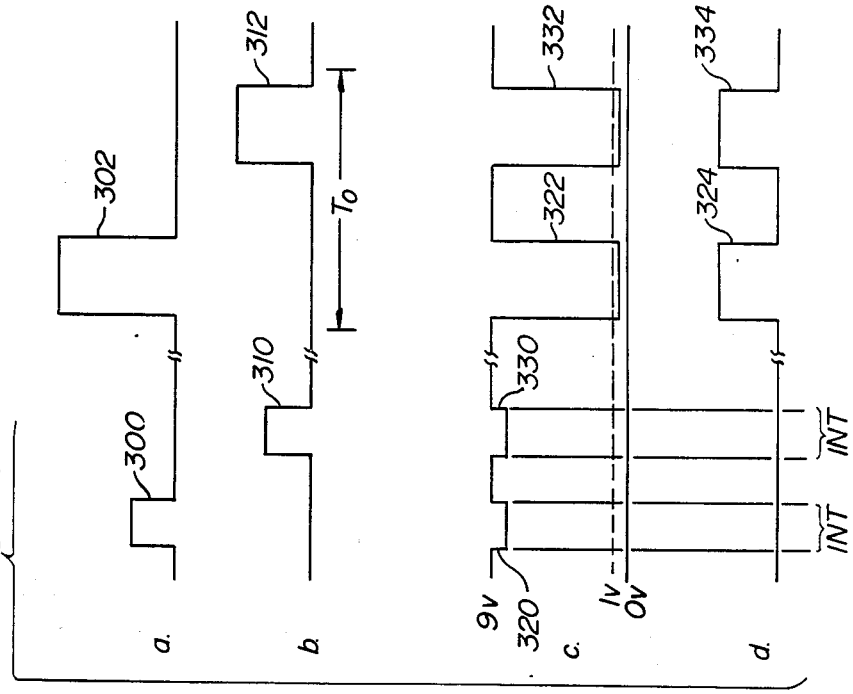

TRANSCUTANEOUS NERVE STIMULATION DEVICE WITH SENTINEL

This invention relates to transcutaneous nerve stimulation devices and, in particular, to sentinels for monitoring electrode connections during use of such devices.

Transcutaneous nerve stimulation devices apply stimulating electrical pulses to electrodes which contact the skin of a patient to relieve pain through electrical nerve stimulation. A patient will generally be given a device by a physician, together with instructions on how to use the device safely and effectively. Thereafter, the patient uses the device to perform the necessary treatment. Accordingly, it is desirable for the device to be simple and safe for the patient to use.

During normal operation of the stimulation device, electrical pulses are applied to the patient's skin through the electrodes. The device will thereby be effectively driving an electrical load or impedance which is the relatively low impedance presented by the patient's skin. However, a patient can be expected to move about during a relatively long treatment period. In fact, stimulation devices of the present invention are manufactured as small, portable units which the patient may carry in a pocket or on a belt. These devices are thus designed so that treatment may proceed while the patient engages in normal daily activities.

In the course of this use of the device, it is quite possible for an electrode to become loose from its normal firm contact with the patient's skin. Under these conditions, several events may occur. The patient may notice that he or she is no longer experiencing the desired pain relief, and may believe that further relief can be gained by increasing the pulse energy. The patient may then increase the energy of the output pulses. Alternatively, the stimulation device may sense the increased impedance presented at the loosened electrode, and may respond by automatically boosting the output signal level.

In either case, the stimulation device will be producing higher energy pulses than desired. Should the loose electrode then come into sudden firm contact with the patient's skin, the patient will receive a sudden and sometimes painful shock as the high energy pulses are applied to the skin.

To prevent these painful shock hazards, some stimulation devices employ a so-called sentinel circuit. A conventional sentinel circuit will continuously monitor the output signal level. Should a rapid change in output signal amplitude occur, the sentinel circuit will detect the occurrence through pulse integration, threshold detection or similar methods. At some predetermined point in the output level change, the sentinel will trigger a warning indicator or shut down the device to alert the user to the hazardous operating condition.

Sentinel operation can be flawed, however, by the variables which can differ from patient to patient. Different patients can have different skin impedances, and can require treatment pulses of varying levels. Moreover, the levels at which pulses become hazardous can vary from patient to patient. To err on the side of safety, it may be necessary to set a detection threshold for the sentinel circuit at which the circuit will produce false triggering during normal operation with certain patients. Such false triggering and needless device shutdowns can be a considerable inconvenience to patients requiring higher energy treatment pulses.

In accordance with the principles of the present invention, a sentinel system is provided in a stimulation device in which a specially tailored sentinel pulse is produced prior to the production of an output pulse for nerve stimulation. The output response to the special sentinel pulse is detected, and a warning signal is produced if the detected response exceeds a threshold level in a given sense. In a preferred embodiment of the present invention, the stimulation device only responds to warning signals occurring substantially during the interval of sentinel pulse production.

In the drawings:

FIG. 1 is a schematic illustration of a stimulation device constructed in accordance with the principles of the present invention;

FIGS. 2, 3, and 4 are more detailed schematics of the illustration of FIG. 1;

FIG. 5 is a block diagram of the microprocessor controller of FIG. 1;

FIGS. 8A, 8B, 9 and 10 are timing diagrams illustrating the operation of the sentinel system of the present invention.

Figure 1:
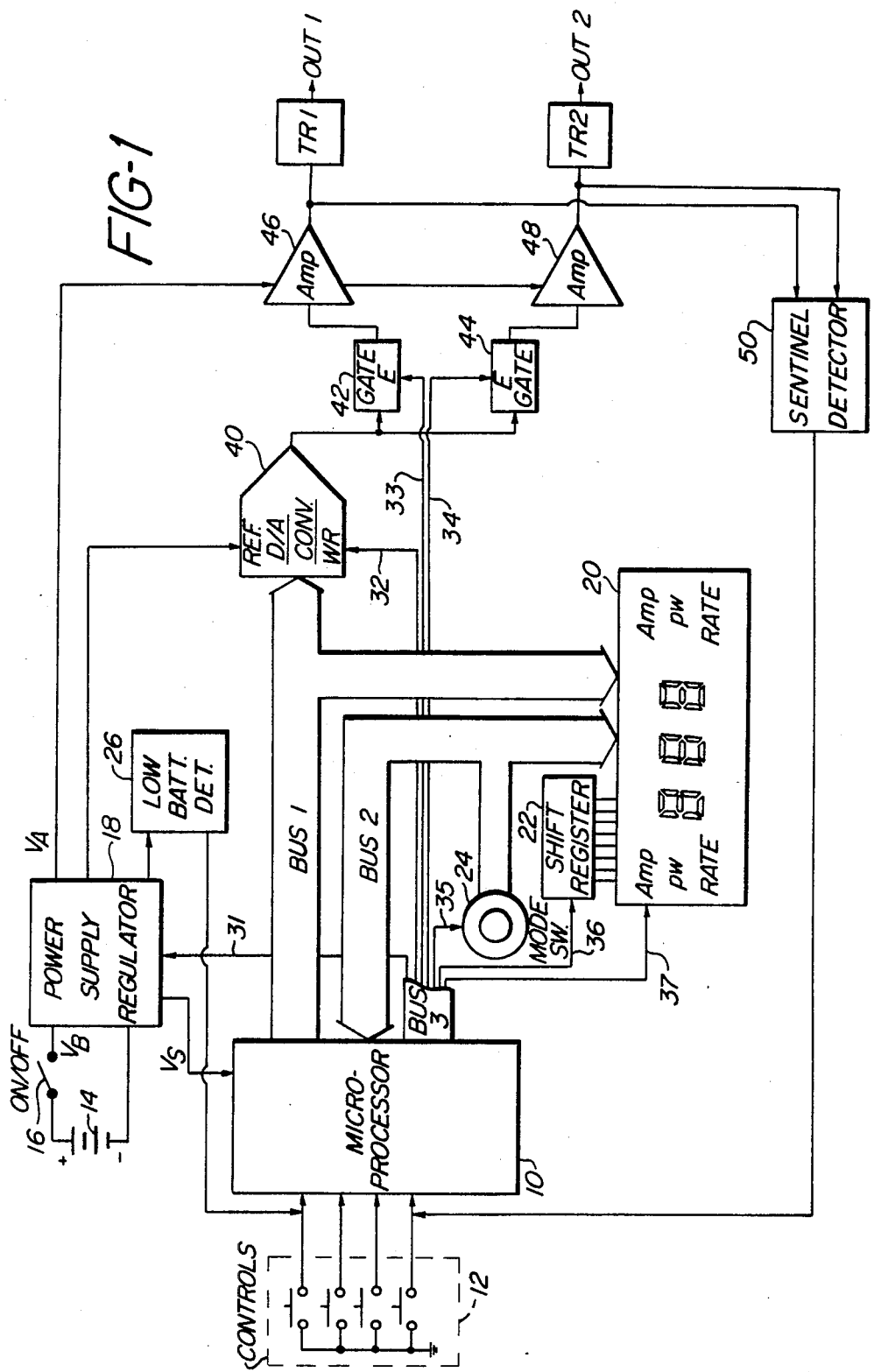

Referring to FIG. 1, a schematic illustration of a digitally-controlled stimulation device constructed in accordance with the principles of the present invention is shown. A microprocessor 10 receives operator input control signals from pushbutton switches shown at 12. The microprocessor also receives inputs from a low battery detector 26 and a sentinel signal detector 50. Signals from either of these two latter sources will precipitate a termination of output pulse production.

The device is powered by a battery 14, which is connected to a power supply regulator 18 by an on/off switch 16. The regulator 18 provides regulated supply voltage $V_S$ for the microprocessor 10, output stage voltage $V_A$, and a reference voltage for a digital-to-analog (D/A) converter 40. The regulator is also coupled to the low battery detector 26 for voltage sampling by the detector.

The microprocessor 10 has two ports and a data bus, shown as bus 1, bus 2, and bus 3. Bus 1 provides digital words representative of output signal levels to the D/A converter 40, and also control signals for segments of the right-most digit of a display 20. Bus 2 provides control signals for segments of the center digit of the display 20, and also samples the setting of a mode switch 24. Bus 3 has a plurality of data lines for dedicated control functions. Line 31 controls the timing of the application of the reference voltage to the D/A converter 40. Line 32 controls the clocking of an output voltage level word into the buffer of the D/A converter. Lines 33 and 34 control the closings of gates 42 and 44, which couple the voltage from the D/A converter to the outputs of the device. Line 35 applies a signal to the mode switch 24 during the time that the state of the mode switch is sampled. Line 36 applies input data to a shift register 22, and line 37 turns on the AMP indicator on the left side of the display 20 when the amplitude of pulses at the first output is being displayed.

The output of the D/A converter is coupled by way of the two CMOS gates 42 and 44 to inputs of output signal amplifiers 46 and 48. The outputs of the amplifier 46 and 48 are coupled to respective output transformers TR1 and TR2, and to inputs of the sentinel signal detector 50.

Figure 2:
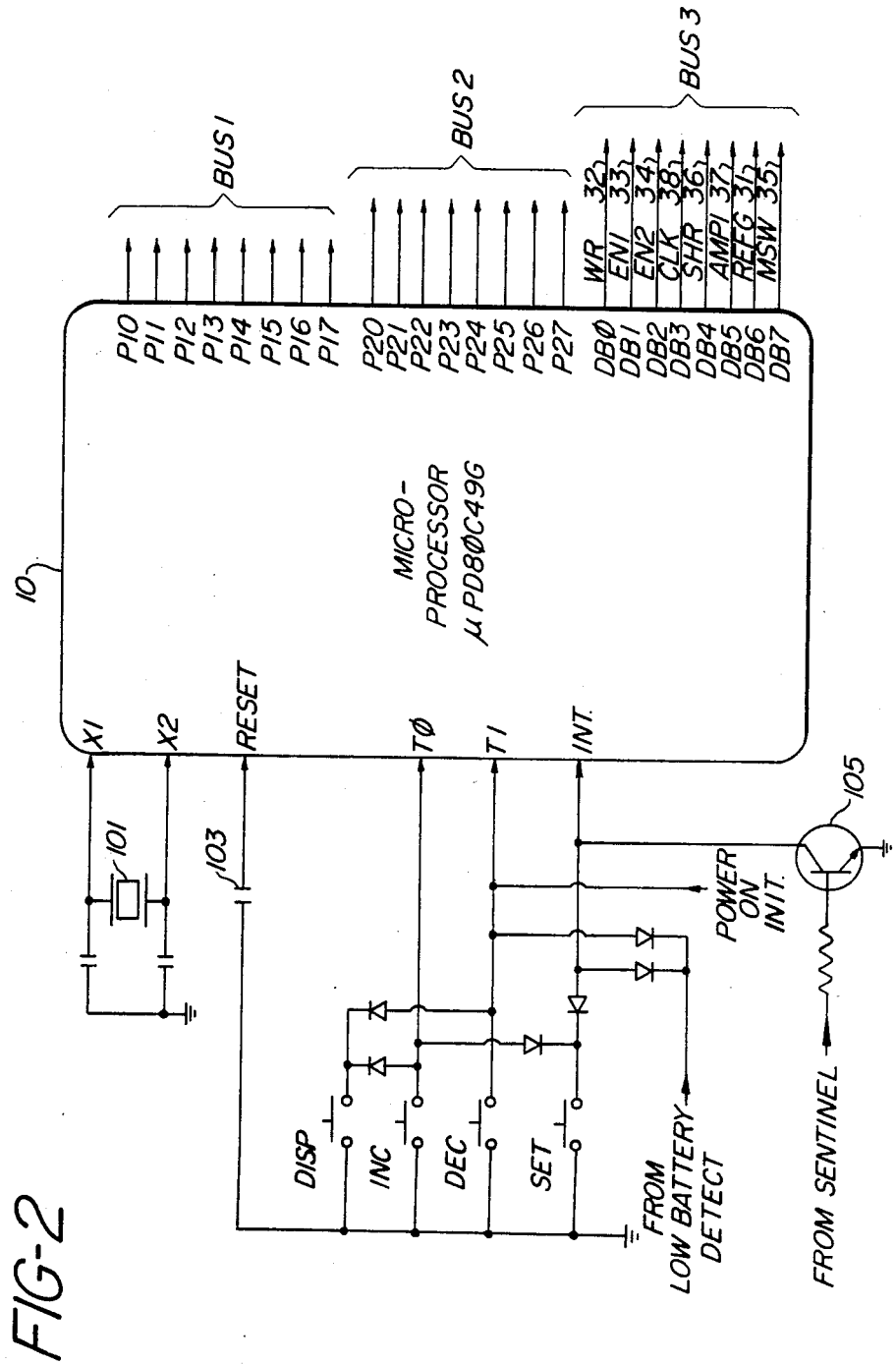

A portion of the schematic diagram of FIG. 1 is shown in further detail in FIG. 2. The microprocessor 10, which may be of the generic type designated 80C49, is shown with its inputs and outputs specifically designated. A 3 MHz crystal 101 is coupled across inputs X1 and X2 of the microprocessor 10. A capacitor 103 couples the reset input of the microprocessor to ground so that the microprocessor will receive a reset command immediately after the device is turned on and the supply voltage has stabilized. Four pushbutton controls, labelled DISP, INC, DEC and SET are coupled to inputs T$\phi$, T1 and the interrupt input of the microprocessor. A number of diodes are used to encode signals from the pushbutton switches. For instance, when the DISP pushbutton is closed to change the function being displayed on the display, the diodes from the DISP pushbutton apply low (ground level) signals to the T$\phi$ and T1 inputs. The microprocessor will then decode these two low lines as a DISP command. Also coupled to microprocessor inputs are a sentinel signal by way of transistor 105, and a low battery detection signal. A power on initializing signal is coupled to input T1.

The individual lines of the three buses are also shown. Buses 1 and 2 are ports of eight lines each, and bus 3 comprises eight data lines for controlling the specific functions enumerated above. Line 38, which was not shown in FIG. 1, is a clock line which is selectively activated to load data from line 36 into the shift register 22.

Figure 3:
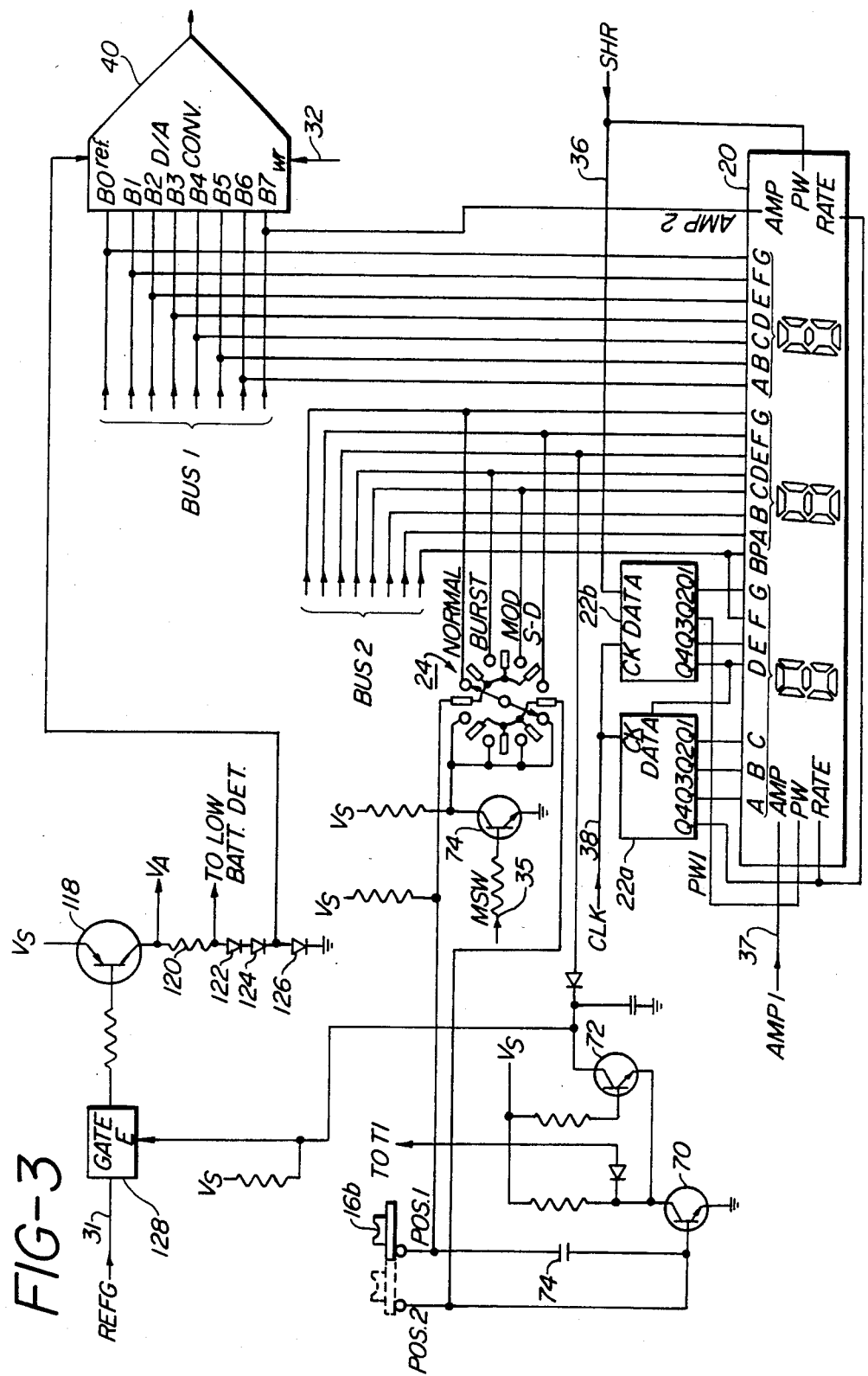

FIG. 3 illustrates the display and bus arrangement of FIG. 1 in further detail. Line 31 from the microprocessor is coupled through a CMOS gate 128 to the base of a transistor 118. A signal REFG on this line 31 turns on transistor 118 to apply a reference voltage to D/A converter 40 when needed during activation of the D/A converter. When the D/A converter is not supplying an output voltage, the reference voltage is not needed and is turned off by the REFG signal to conserve battery power. The reference voltage is otherwise turned on momentarily every half second to sample the battery voltage. The gate 128 will be interrupted momentarily after the on/off switch 16 is turned on while capacitor 74 charges. The time for the capacitor to charge allows the system to stabilize before transistor 70 is turned off, at which time the T1 input of the microprocessor is released. When T1 is released, the output pulses are at a low, safe level. Transistor 72 in turn will turn off, releasing the enabling line to gate 128. Transistor 72 also forces a mode change to the desired mode. The application of reference voltage to the A/D converter may then proceed, as the microprocessor is running with valid data. This hold-off sequence prevents the application of inaccurate, high-level output pulses to the patient after a momentary turning off of power, which could leave spurious data in the microprocessor registers until the registers have been validly restored.

When the mode switch 24 is to be interrogated to determine if a change in mode has occurred, a signal MSW on line 35 momentarily turns on a transistor 74. The arm of the mode switch 24 will then apply a low signal level to the output of the switch to which it is presently connected. This low signal level is detected on the corresponding one of the four lines of bus 2 to which the mode switch is connected. Bus 2 is acting as a data input port at that time. During the remainder of the time, bus 2 is providing segment drive signals for the middle digit of the display 20 and a backplane (BP) signal. Bus 1 is providing segment drive signals for the right-most digit of the display at all times except when the D/A converter 40 is being loaded with output signal level data.

Shift register 22, which is comprised of two four-bit, serially connected shift registers 22a and 22b, is loaded with data for the left-most display digit from line 36. The clock signal on line 38 shifts the data into the shift registers 22a, 22b. The display also displays the indicators AMP, PW, and RATE on either side to tell the operator which parameter is being controlled by the INCREASE and DECREASE pushbuttons. The left indicators correspond to output 1 and the right indicators to output 2. The AMP indicator for output 1 is controlled by the AMP1 signal on line 37, and the AMP indicator for output 2 is controlled by one line of bus 1. The PW (pulse width) indicator for output 1 is controlled by the Q2 location of shift register 22b, and the PW indicator for output 2 is time-shared on line 36. The RATE indicators are commonly controlled by the Q4 location of shift register 22a, as both outputs will exhibit the same pulse rate, or frequency.

Figure 4:
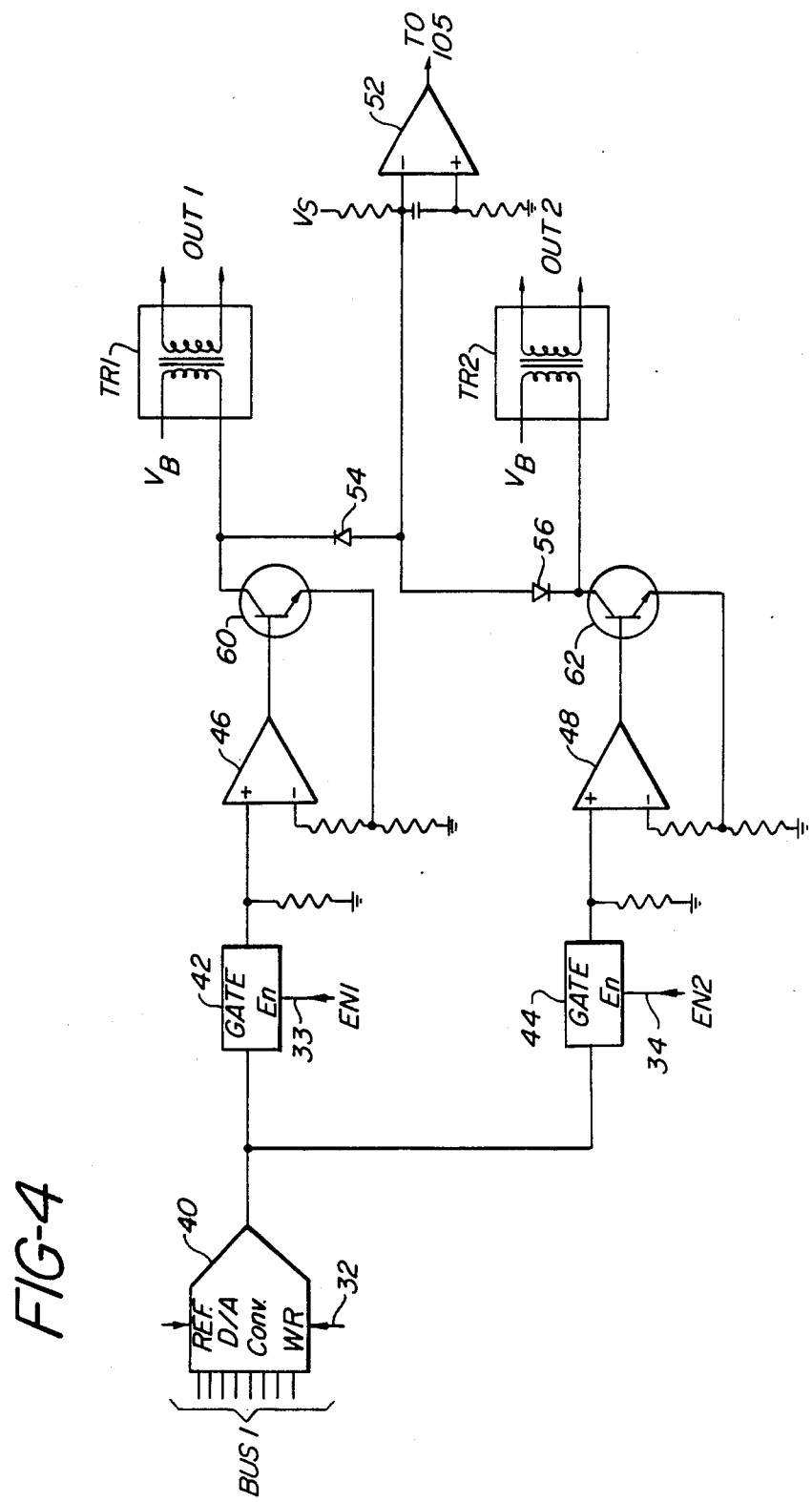

The output section of the stimulation device is shown in detail in FIG. 4. When the D/A converter is producing the desired output level, signals EN1 and EN2 on lines 33 and 34 render CMOS gates 42 and 44 conductive for periods corresponding to the operator-entered pulse width settings. Output pulses are then applied to amplifiers 46 and 48. Output transistors 60 and 62 are turned on to apply output signals to output transformers TR1 and TR2. The output pulses are then transformer coupled to leads connected to electrodes (not shown) on the skin of the patient.

In accordance with the principles of the present invention, test pulses called sentinel pulses are transmitted before each transmission of output pulses. The sentinel pulses verify that the electrodes are properly connected to the patient. If the connections are properly made, the pulses will not exceed the trigger threshold of a comparator 52, and the output state of the comparator will not change. Improper electrode connections will cause detection of the sentinel pulses, which are coupled to the interrupt input of the microprocessor by transistor 105 (FIG. 2), and the microprocessor will be informed of the improper connections. The microprocessor will query its interrupt line during sentinel pulse transmission, and will recognize the problem. A sentinel flag will be set, and the system will halt the production of output pulses until the failure is remedied and the device is restarted.

The software which controls the microprocessor, and hence operation of the device, is stored in a 2K read only memory (ROM). The software is partitioned into a foreground program and a background program. The two programs interact through an exchange of data words and flag bits stored in 128 bytes of random access memory (RAM). This software/hardware structure is shown in FIG. 5. During most of the time, the background program loop is running. The background program continuously monitors the pushbutton inputs and the mode switch, looking for a change. When a change occurs, it is detected and any variables which require change are calculated and stored in the RAM. The variables are then available for use by the foreground program.

An internal timer which runs continuously interrupts the background program every 2.5 msec. The foregound program, which controls precise timing functions, then proceeds through its sequence, producing output signals at the appropriate times. Output signals are produced in accordance with the data values that the foreground program finds in RAM locations. When the foreground program produces output signals from new data values it returns status flags to the RAM to indicate to the background program that the new data has been utilized.

Figure 6A:
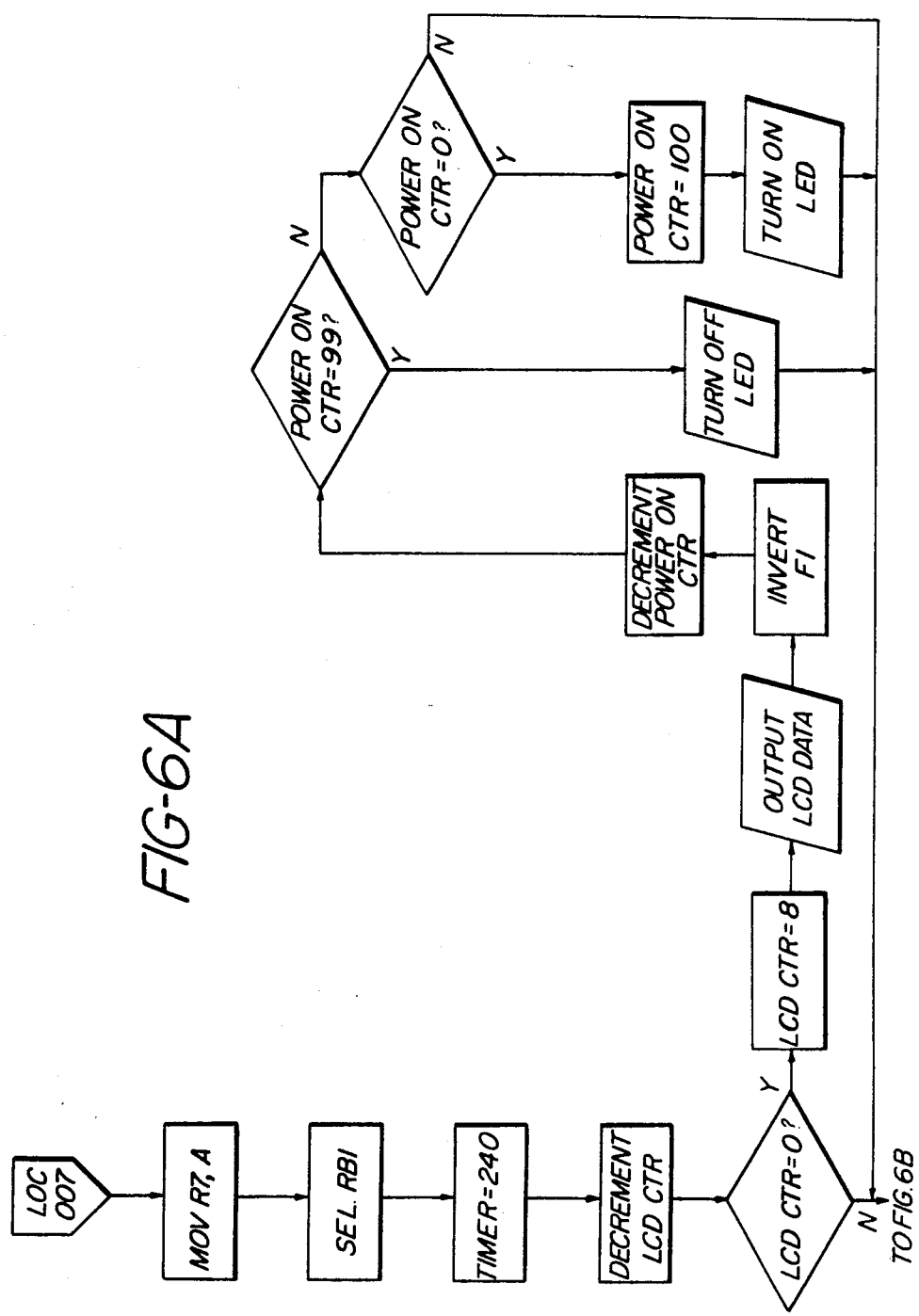
FIGS. 6A, 6B, 6C and 7 are flowcharts of the programming of the microprocessor controller of FIG. 5.
Figure 6B:
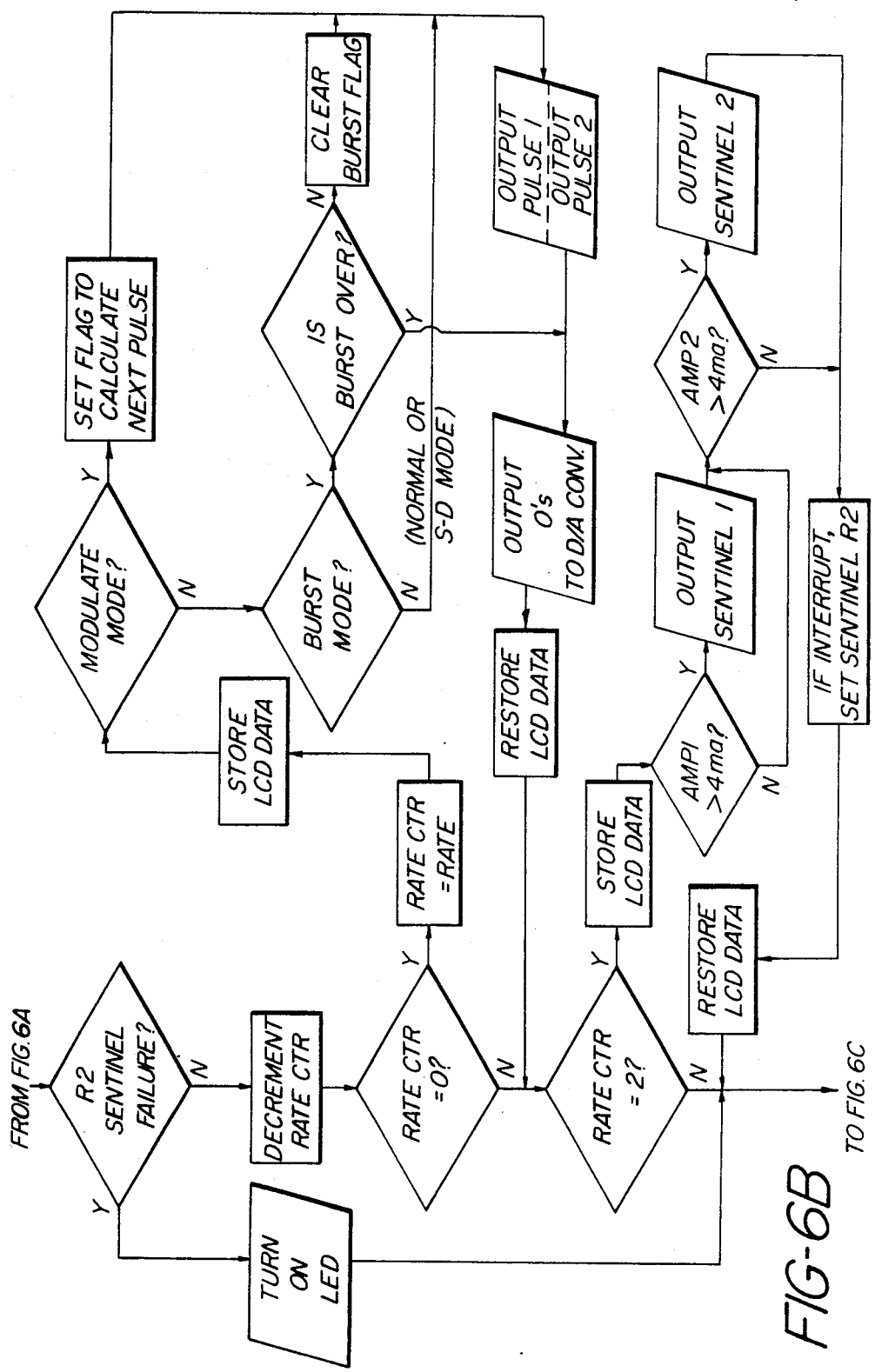
Figure 6C:
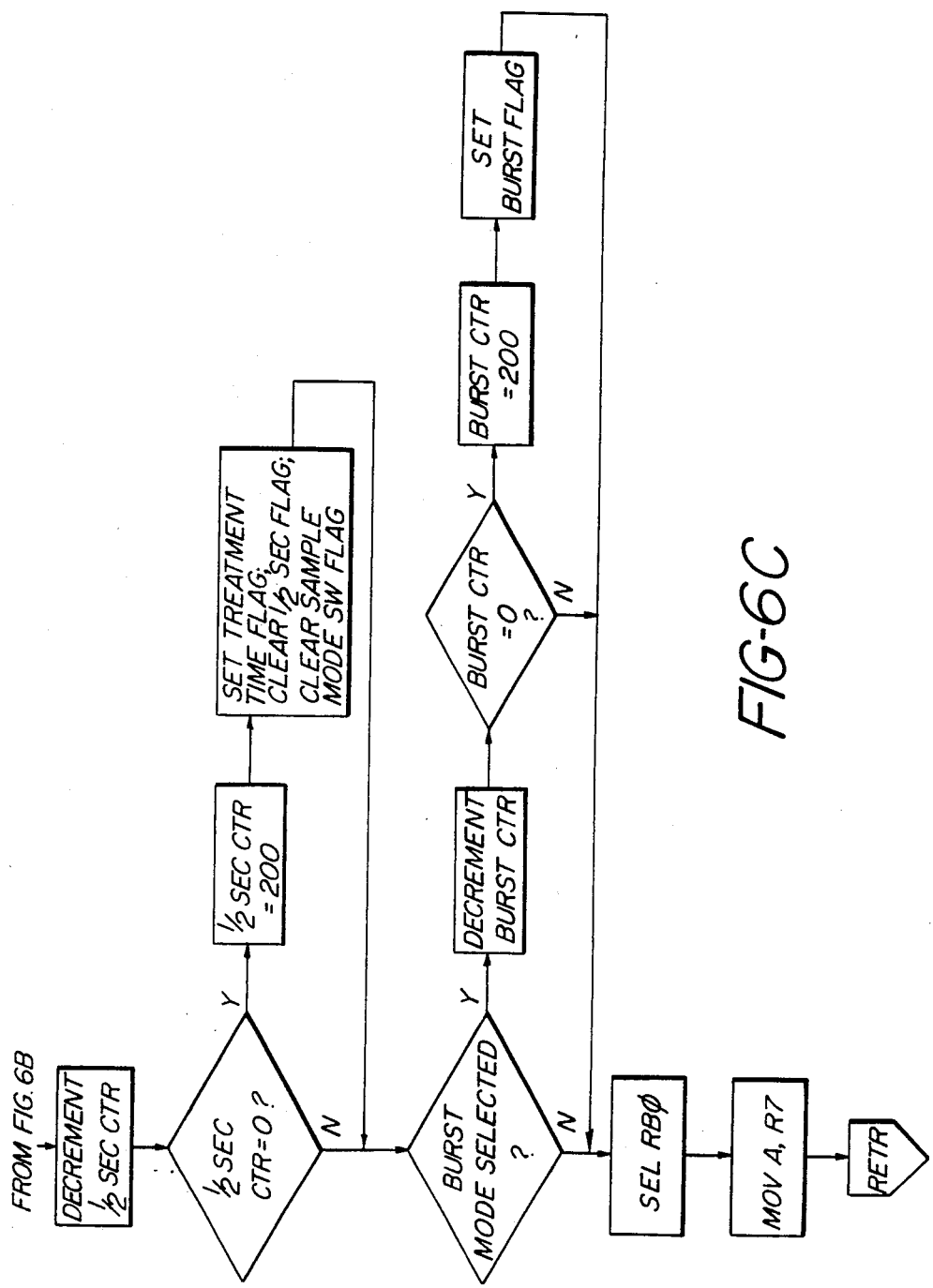

The foreground program is shown in flowchart form in FIGS. 6A, 6B, and 6C. When the internal timer has reached zero after 2.5 msec, the background program is interrupted and the microprocessor goes to location 007, where the foreground program begins. The background program data in the accumulator is stored in register 7, and register bank 1 is selected for foreground program control. Register bank 1 contains a number of counters which are decremented by the foreground program to maintain the appropriate timing of output functions. The internal timer is initialized to a value of 240, corresponding to 2.5 msec, and the foreground processing begins.

The foreground program first decrements an LCD counter for control of the display. The LCD display receives two types of pulse trains: a common backplane pulse train and individual segment pulse trains, each of a frequency of 25 Hz. When the two pulse trains are changing in phase for any one display segment or indicator, there is no potential difference between the pulse trains and the segment or indicator is not displayed. When the two pulse trains are in phase opposition, however, there is always a voltage differential between them and the segment or indicator will be displayed.

When the LCD counter has been decremented to zero, a half cycle of the 25 Hz pulse rate has expired and the outputs to the LCD display must be changed. The LCD counter is initialized to a value of eight (8 times 2.5 msec=20 msec=½ cycle of 25 Hz), and LCD data resident in the RAM is put on buses 1 and 2. LCD data is serially loaded into the shift register 22 from data line 36. An invert flag F1 is set to inform the background program that it must calculate inverted LCD data values for the next half cycle (opposite phase) of the LCD pulse trains.

A Power On counter is decremented. Every two seconds a "power on" LED (light emitting diode) is flashed for 20 msec to indicate to the operator that the device is operating properly. The counter is first checked for a value of 99. At this value, the LED is turned off. The counter is then checked for a value of zero, at which time the LED is to be turned on. At zero the counter is reinitialized to a value of 100, the LED is turned on, and the foreground program continues in FIG. 6B.

A register R2 is then checked to see if a sentinel failure has been detected. If so, the LED is turned on continuously to alert the user of the problem. The LED can only be turned off by remedying the electrode problem and restarting the system.

The program next decrements the rate counter. The rate counter counts down from an initial value (RATE) which is a number calculated by the background program. The RATE number represents the interval between output pulses selected by the operator. If the rate counter has reached zero, output pulses are to be produced, and the counter is reinitialized and the LCD output data is stored. Since bus 1 will now be used for output data, the LCD data on that bus must be stored during this time, and restored on the bus after the output pulse sequence is finished.

The program first checks to see if the device is operating in the modulate mode. In this mode, each output pulse differs in pulse width and amplitude from the previous pulse. Hence, a flag is set to inform the background program that a pulse has been produced, and that new parameter values must be calculated for the following pulse. If the device is not in the modulate mode, the program checks to see if the device is in the burst mode. In the burst mode, a burst of seven pulses is produced every half second at a rate of 80 Hz. The amplitude of the burst pulses is determined by the operator. If the device is in the burst mode, the program checks to see if a pulse sequence is in progress. If the burst pulse sequence is over, no output is produced. If the sequence of seven pulses is not complete, a burst mode flag is cleared and pulse output commences.

When the program does not find the device to be operating in either the modulate or burst mode, the device must be operating in either the normal or the strength-duration mode. In either case, a repetitive sequence of treatment pulses is to be produced, and the program proceeds to produce output pulses.

The microprocessor controls pulse production at the first output, then pulse production at the second output. At first, a REFG signal on line 31 applies a reference voltage to the D/A converter. A digital word is put on bus 1, and is loaded into the D/A converter buffer by a WR signal on line 32. An EN1 signal on line 33 then renders gate 42 conductive for the desired duration, or pulse width, and the output signal is produced at the first output. The program then loads a new pulse amplitude value into the D/A converter, and the gate enabling sequence is performed on gate 44 to produce the selected pulse at the second output. After pulse output is complete, the REFG signal is dropped, and all zeroes are loaded into the D/A converter. The LCD data is restored on bus 1 for the display, and the foreground program continues. Pulse output comprises a major portion of the foreground program's time, since output pulses can range from 30 to 250 microseconds in duration.

The program next checks to see if the count of the rate counter is two. If so, sentinel pulses must now be produced, in advance of the output pulses five milliseconds later. Again, the LCD data on bus 1 is stored so that bus 1 can be used to transfer pulse amplitude values to the D/A converter. The program checks to see if the amplitude of the upcoming pulse for the first output will be greater than 4 milliamperes as referenced to an internal milliampere scale. If not, no sentinel is needed, since the output pulses themselves are too low to result in any patient hazard. But if the output pulse is to be greater than 4 ma., a sentinel pulse with a 5 ma. amplitude and a 30 $\mu$sec. duration is produced at the first output, using the same output sequence described above. This process is repeated to generate a sentinel pulse at the second output.

If an electrode has come loose from the patient as detected by the comparator 52, an interrupt will have occurred at the INT input. If the interrupt has occurred, a sentinel-detected failure flag is set in a register R2. During the following pass through the foreground program, this flag in register R2 will be detected, the LED will be turned on, and the output pulse sequence will be bypassed.

Continuing on in FIG. 6C, a ½ second counter is decremented. A number of functions occur at half-second intervals. If the ½ second counter is at zero, it is reinitialized and a treatment time flag is set. During treatment, the patient sees treatment time on the display in elapsed time up to 255 minutes. Treatment time is accumulated in half-second intervals by the background program in response to the setting of the treatment time flag.

A half-second flag is also cleared. To prevent a patient from producing needlessly high amplitude pulses by ramping the output pulse amplitude up too quickly, the pushbuttons that permit the pulse parameters to be changed are allowed to produce a step change only once each half-second. This half-second flag allows these time increments to be monitored by the background program. When a parameter pushbutton is held down, the parameter will change by one increment every half second.

A sample mode switch flag is also cleared. This flag tells the background program to interrogate the mode switch every half second. More frequent interrogation has not been found to be helpful or necessary, and in fact reduces the time during which other functions may be performed.

After the ½ second counter is queried, the mode is again checked to see if the burst mode has been selected. If it has, the burst counter is decremented and checked to see if it is at zero. If so, it is reinitialized and the burst flag is set so that a new sequence of seven burst pulses will be produced beginning with the next pass through the foreground program.

The foreground program is now completed, and the register bank φ for the background program is selected. The accumulator is restored to the contents it had at the beginning of the foreground sequence, and the system resumes with the background program at the point where it was before the foreground timer interrupt occurred.

Figure 7:
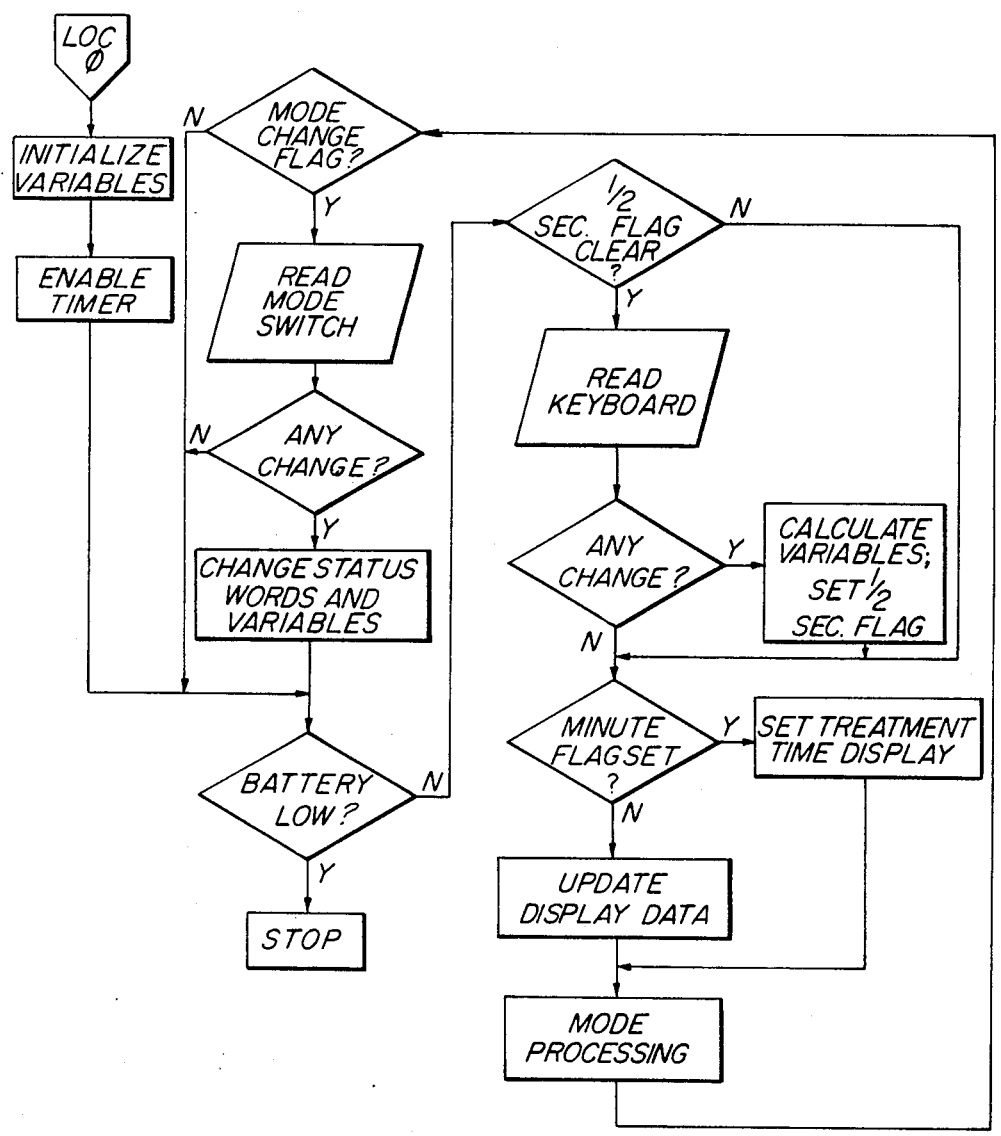

The background program is shown in the flowchart of FIG. 7. When the stimulation device is turned on, the microprocessor is reset and the background program starts from location zero. Several variables are initialized; pulse amplitude is set to zero, pulse width is set at 50 μsec., and the rate is set at 80 Hz. The sentinel is cleared and counters are initialized. The internal timer for the foreground program is enabled with its initial count of 240.

The background program then checks the battery voltage. If it is low, the program stops and the LED is lit. The background program also checks to see if a sentinel failure has occurred, and if the LED has been lit. If so, the program will stop. If the battery voltage is at a sufficient level and there is no sentinel failure, the program checks to see if the one-half second flag has been cleared by the foreground program. If the flag has been cleared, the background program reads the keyboard buttons DISP, INC, and DEC, and looks for any change, If the flag has not yet been cleared, a half second has not passed since the last button was pushed, and the keyboard is not read. If a new button entry is detected, the program decodes and notes it, and calculates the appropriate new variables for storage in the RAM. After this calculation, the one-half second flag is reset, to be cleared by the foreground program after one-half second has been counted down.

The background program then checks to see if a minute flag has been set. During treatment, the program records and display treatment time in minutes. Treatment time is tracked in one-half second increments. When a full minute has been accumulated, the treatment time display is incremented to the next minute, up to a maximum of 255 minutes. During treatment this time is flashed periodically to inform the user that treatment is progressing normally. The off time during flashing extends the life of the display.

After the minute flag is checked and found not to be set, the data for the LCD display is calculated and loaded into the appropriate locations in the RAM for access by the foreground program. As mentioned above, the LCD display waveforms must be inverted every 20 msec, in synchronism with the change of state of the LCD backplane pulse train of 25 Hz.

Thereafter, the background program does processing necessary according to the mode of operation. If treatment is proceeding in the normal or the strength-duration mode, the program proceeds to the mode interrogation sequence of the program. If the device is in the burst mode, the program checks to see if the burst sequence of seven pulses has been completed. If the device is in the modulation mode, the program calculates the parameters of the next pulse if the appropriate flag has been set by the foreground program. If the device is in the calibration portion of the strength-duration mode, the program calculates any needed pulse widths, amplitudes, and the logarithmic curve for pulse characteristics. After these calculations, the program proceeds to the mode interrogation sequence.

The modulation and strength-duration modes of operation are more fully described in concurrently filed U.S. patent application Ser. No. 617,444, filed June 5, 1984, "TREATMENT PULSE SEQUENCES FOR A TRANSCUTANEOUS NERVE STIMULATION DEVICE."

The background program next checks to see if the sample mode switch flag has been cleared by the foreground program. If it hasn't, the program drops down to the battery check step. If the flag has been cleared, the program reads the mode switch. If there has been a mode change, the program changes any status words for the mode processing sequence, including the flag, and initializes variables for parameter values. The background program then proceeds to the battery and sentinel check step.

It should be remembered that the foreground program is continually interrupting the background program every time the internal timer counts an interval of 2.5 milliseconds.

In FIGS. 8A and 8B, timing diagrams are shown depicting operation of the sentinel system during normal electrode placement. In this example, the stimulation device has been set to produce eighty pulses per second continuously, the NORMAL mode of operation. At the eighty pps rate, the RATE counter is loaded with a value of five. Thus, every five passes through the foreground program, an output pulse will be produed (5 times 2.5 msec=12.5 msec=80 pps).

At the top of FIG. 8A, the RATE counter value is shown. At the count of two, five milliseconds before the next output pulse sequence, the foreground program will execute the sentinel pulse instructions. The REFG signal applies a reference voltage to the D/A converter 40 (FIG. 4) for the duration of the sentinel pulse sequence. A first WR pulse 202 on line 32 loads an amplitude value data word 212 equal to a 5 ma. amplitude into the D/A converter from bus 1. The LCD display data is restored to the bus 1 and an EN1 signal on line 33 closes gate 42 for 30 μsec. The sentinel pulse 230 is produced at this time at the first output (TR1).

A second WR pulse 204 then loads a 5 ma. data value 214 into the D/A converter from bus 1. The LCD display data is restored on bus 1 while an EN2 signal on line 34 closes gate 44 to produce a 30 μsec sentinel pulse 232 at the second output (TR2). Finally, a zero value data word 216 is loaded into the D/A converter, the REFG pulse ends, and the sentinel sequence is finished.

During the next pass through the foreground program the RATE counter is decremented to one. On the following pass the RATE counter is decremented to zero, then reset to five and an output pulse sequence is executed. The output pulse sequence proceeds in the same fashion as the sentinel pulse sequence. A first WR pulse 203 loads the amplitude value 213 for the first output pulse into the D/A converter from bus 1. The REFG signal applies the reference voltage to the D/A converter and the LCD display data is restored to the bus 1. The EN1 signal on line 33 closes gate 42 for the chosen pulse width duration to produce an output pulse 220 for the first output. When the output pulse 220 has ended, a second WR pulse 205 loads the amplitude value 215 for the second output pulse into the D/A converter. The LCD display data is again restored to the bus 1 and the EN2 signal on line 34 closes gate 44 for the duration of the second output pulse 222. Finally a WR pulse 207 loads a zero value data word 217 into the D/A converter, the REFG pulse ends, and the output sequence is completed with the restoration of the LCD display data on bus 1.

The sentinel and output pulse sequence intervals are related to the LCD display data waveforms in FIG. 8B. The LCD display is continuously receiving a backplane square wave BP of 25 Hz at the BP input of the display (FIG. 3). This 25 Hz square wave is seen to change polarity every 20 msec. The display waveforms on bus 1 are changing polarity with the BP waveform. Display segments which are not being displayed receive an in-phase square wave as indicated by the dashed waveform on bus 1. The solid bus 1 square wave is applied to display segments that are to be displayed.

The sentinel pulse intervals S and the output pulse intervals T on bus 1 recur every 12.5 msec for the 80 pps rate. These intervals occur asynchronously with respect to the display waveform transitions. The sentinel intervals S occur 5 msec before each output pulse interval T. Below the bus 1 timing diagram the count of the RATE counter is shown for one RATE counter cycle.

FIGS. 9 and 10 depict the operation of the sentinel detector of FIG. 4 during periods of proper and improper electrode connection, respectively.

In FIG. 9a, a sentinel pulse 300 and an output pulse 302 for the first output are shown. These pulses are applied to the base of transistor 60 in FIG. 4. A sentinel pulse 310 and an output pulse 312 for the second output are shown in FIG. 9b. These pulses are applied to the base of transistor 62 in FIG. 4. Below the output pulses 302 and 312 the output pulse interval $T_o$ is indicated.

Transistor 60 and 62 are normally turned off with a battery voltage $V_B$ appearing on their collectors. The sentinel and output pulses will cause the transistors to turn on in varying degrees. The collector voltages will then be a function of the load impedances at the electrodes of the stimulation device. When properly connected, low impedances will appear across the electrodes, and sentinel pulses 300 and 310 will cause the transistors to conduct toward saturation as shown by corresponding pulses 320 and 330 in FIG. 9c. The levels of pulses 320 and 330 are above the one volt threshold needed at the inverting input of amplifier 52 to cause the amplifier to change its output state. Thus, no pulses will be produced by the detecting amplifier 52 during the occurrence of pulses 320 and 330, as shown in FIG. 9d. During the production of the sentinel pulses 300 and 310 the microprocessor is responsive to signals on its interrupt line INT (FIG. 2). But when pulses 320 and 330 do not fall below the one volt threshold, no interrupt signals are produced by amplifier 52.

During the occurrence of output pulses 302 and 312, transistors 60 and 62 may produce pulses below the one volt threshold, as indicated by pulses 322 and 332. These pulses will cause the amplifier 52 to produce pulses 324 and 334 as the one volt threshold is exceeded by the negative-going pulses 322 and 332. However, the microprocessor is not responsive to interrupts at its INT input during the output pulse sequence, and the stimulation device continues to operate.

FIG. 10a shows a sentinel pulse 400 for the first output, and FIG. 10b shows a sentinel pulse 410 for the second output. In this example, the first output electrode is assumed to have come loose. Thus, transistor 60 will see a high output impedance on the order of 15,000 to 40,000 ohms. The sentinel pulse 400 will drive transistor 60 sharply toward saturation, and the negative-going voltage swing of the collector of transistor 60 will exceed the one volt threshold, as indicated by pulse 420. The amplifier 52 will therefore change state to produce an output pulse 450 during sentinel pulse 400. Since the microprocessor is responsive to pulses at its interrupt intput INT at this time, a sentinel failure will be noted by the microprocessor in response to pulse 450. A sentinel failure word is stored in register R2 by the foreground program. During the next execution of the foregound program at time $t_s$, the LED will be lit and the output pulse sequence will be continuously bypassed until the electrode is properly reattached to the patient and the stimulation device is restarted.

Sentinel pulse 410 is applied to transistor 62, which is driving a properly attached electrode in this example. Thus, the collector voltage of transistor 62 will not drop below the one volt threshold of amplifier 52, as indicated by pulse 430 in FIG. 10c. Accordingly, amplifier 52 will not change state in response to sentinel pulse 410 and pulse 430. However, no output pulses will be produced at either output during the output pulse interval $T_O$ once a sentinel failure has been detected.

In use of the stimulation device of the present invention, a user places the electrodes on the treatment area of the body. The desired mode is selected by setting the mode switch, and the ON/OFF switch is turned on. The left AMP indicator for output 1 is displayed first, and the user then increments (INC) or decrements (DEC) the pulse amplitude value using the appropriate buttons. The DISP button is pressed and PW for the first output is displayed. The user then pushes the INC and DEC buttons to set the desired pulse width. A further push of the DISP button displays the RATE indication, and the INC and DEC buttons are pressed to set the desired pulse rate. The DISP button is pressed two more times and the amplitude and pulse width for the second output are displayed and adjusted in the same manner. The pulse rate is common to the two outputs.

The amplitude values are calibrated over a range of 0–50 ma., and can be incremented and decremented in 1 ma. steps. The pulse width is variable over a range of 30–250 microseconds in steps of 10 microseconds. The rate is variable from two to one hundred Hertz, with selections being 2 Hz, 100 Hz, and 10–80 Hz in steps of 10 Hz.

What is claimed is:

1. In a transcutaneoud nerve stimulation device, including means for producing, at an output, therapeutic electrical stimulation pulses; a sentinel system for detecting improper electrode connection comprising:
   means for producing a sentinel pulse at said output prior to the production of a stimulation pulse;
   means, coupled to said putput, for detecting the response at said output during the production of said sentinel pulse;
   means, coupled to said detecting means, and selectively activated during the production of a sentinel pulse, for terminating the production of stimulation pulses at said output following the detection of an undesired response to said sentiel pulse.

2. In the transcutaneous nerve stimulation device of claim 1, wherein said stimulation pulse production, said sentinel pulse production, and said stimulation pulse termination means all comprise a microprocessor during different times of microprocessor operation.

3. In the transcutaneous nerve stimulation device of claim 2, wherein said output response detecting means comprises a comparator having a first input coupled to said output, a second input coupled to a reference level, and an output coupled to an input of said microprocessor.

4. In the transcutaneous nerve stimulation device of claim 1, further including means for producing stimulation pulses at a second output; wherein said sentinel pulse production means produces a sentinel pulse at said second output prior to the production of a stimulation pulse at said second output; and wherein said response detecting means is further coupled to said second output.

5. The sentinel system of claim 1, wherein said detecting means includes an amplifier having a first input coupled to said output and a second input coupled to receive a reference signal, said amplifier producing a detection signal at an amplifier output when a signal at said first input exceeds a threshold level in a given sense.

6. The sentinel system of claim 5, wherein said detecting means includes a microprocessor having an input coupled to said amplifier output, said microprocessor being responsive to said detection signals during the production of a sentinel pulse for the production of a sentinel indication signal.

7. The sentinel system of claim 6, wherein said microprocessor is not responsive to detection signals at said amplifier output during the time of production of a stimulation pulse.

* * * * *

UNITED STATES PATENT AND TRADEMARK OFFICE
CERTIFICATE OF CORRECTION

PATENT NO. : 4,582,063

DATED : April 15, 1986

INVENTOR(S) : Stanley P. Mickiewicz, Alan Coombes

It is certified that error appears in the above-identified patent and that said Letters Patent is hereby corrected as shown below:

Column 11, line 15 "putput"

should be --output--.

Signed and Sealed this

Third Day of February, 1987

*Attest:*

DONALD J. QUIGG

*Attesting Officer*  *Commissioner of Patents and Trademarks*